(12) United States Patent
Kim

(10) Patent No.: US 8,024,129 B2
(45) Date of Patent: Sep. 20, 2011

(54) METHOD AND APPARATUS FOR SEARCHING GENE SEQUENCE

(75) Inventor: Ki eun Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 1339 days.

(21) Appl. No.: 11/561,479

(22) Filed: Nov. 20, 2006

(65) Prior Publication Data

US 2007/0218473 A1    Sep. 20, 2007

(30) Foreign Application Priority Data

Mar. 17, 2006    (KR) ........................ 10-2006-0024788

(51) Int. Cl.
*G01N 33/48*    (2006.01)
*G06F 7/60*    (2006.01)
*C12Q 1/68*    (2006.01)
*G06G 7/58*    (2006.01)

(52) U.S. Cl. .................. 702/19; 435/6; 702/20; 703/2; 703/11

(58) Field of Classification Search ........................ None
See application file for complete search history.

*Primary Examiner* — Shubo Zhou
(74) *Attorney, Agent, or Firm* — Cantor Colburn LLP

(57) ABSTRACT

A method and apparatus for searching a gene sequence. The gene sequence search method includes receiving the gene sequence from a user, generating extended sequences including the received gene sequence, partial sequences included in the gene sequence and an inverse sequence complementary to the gene sequence, storing the gene sequence, the extended sequences, the partial sequences, the inverse sequence and input-related record information in a database, integrated-searching the gene sequence using a gene sequence search server, estimating a gene sequence search ranking for a predetermined period using the database and outputting an integrated and searched result of the gene sequence and a gene sequence search ranking result to the user.

22 Claims, 5 Drawing Sheets

FIG. 3

| | QUERY TRANSFER |

Top 10 RANKS

| RANK | Sequence | Hits | Last Query |
|---|---|---|---|
| 1 | ACCAAAGAGTGATACTCA | 17 | 2006-01-24 16:58:08 |
| 2 | ATAAGCTAGCTTGACTGCGAGCG | 16 | 2006-01-24 16:59:53 |
| 3 | TTAAACCT | 9 | 2006-01-24 16:55:00 |
| 4 | CTGCGAGACGGACAAGTCGA | 8 | 2006-01-24 16:56:52 |
| 5 | ACAGGTTGGTCCCTATCTATTGT | 7 | 2006-01-24 16:55:20 |
| 6 | ACCAAAGAGTGATACTCAGGAGA | 5 | 2006-01-24 16:55:37 |
| 7 | CTATCTATTG | 4 | 2006-01-24 16:58:33 |
| 8 | CTTGACTGCGA | 4 | 2006-01-24 17:05:14 |
| 9 | TT | 1 | 2006-01-24 17:53:15 |
| 10 | CT | 1 | 2006-01-24 16:29:32 |

Current search:

FIG. 4

| | | | QUERY TRANSFER |

Top 10 RANKS

| RANK | Sequence | Hits | Last Query |
|---|---|---|---|
| 1 | ACCAAAGAGTGATACTCA | 17 | 2006-01-24 16:58:08 |
| 2 | ATAAGCTAGCTTGACTGCGAGCG | 16 | 2006-01-24 16:59:53 |
| 3 | TTAAACCT | 9 | 2006-01-24 16:55:00 |
| 4 | CTGCGAGACGGACAAGTCGA | 8 | 2006-01-24 16:56:52 |
| 5 | ACAGGTTGGTCCCTATCTATTGT | 7 | 2006-01-24 16:55:20 |
| 6 | ACCAAAGAGTGATACTCAGGAGA | 5 | 2006-01-24 16:55:37 |
| 7 | CTATCTATTG | 4 | 2006-01-24 16:58:33 |
| 8 | CTTGACTGCGA | 3 | 2006-01-24 17:00:25 |
| 9 | TT | 1 | 2006-01-24 17:53:15 |
| 10 | CT | 1 | 2006-01-24 16:29:32 |

Related searchs (CTTGACTGCGA)

| RANK | Sequence | Hits | Last Query |
|---|---|---|---|
| 1 | ATAAGCTAGCTTGACTGCGAGCG | 16 | 2006-01-24 16:59:53 |
| 2 | CTTGACTGCGA | 3 | 2006-01-24 17:00:25 |
| 3 | GCTTGACTGCGAGCG | 1 | 2006-01-24 16:30:40 |

Current search: CTTGACTGCGA

METHOD AND APPARATUS FOR SEARCHING GENE SEQUENCE

This application claims priority to Korean Patent Application No. 10-2006-0024788, filed on Mar. 17, 2006, and all the benefits accruing therefrom under 35 U.S.C. §119, the contents of which are incorporated herein in its entirety by reference.

BACKGROUND OF THE INVENTION

1. Field of the Invention

The present invention relates to a method and apparatus for searching a gene sequence, and more particularly, to a method and apparatus for searching a gene sequence, through which study trends in a biology field can be understood.

2. Description of the Related Art

The Human Genome Project for revealing a complete sequence of human genome is established and thus diagnosis and treatment of intractable diseases using a gene are being significantly developed. The future of so-called Personalized Medicine and Predictive Medicine is opening due to the Human Genome Project.

When genes properly perform their own parts and functions, the human body grows normally, persons can perform his/her functions and maintain his/her life. However, if mutation occurs at even a very small part in a gene and thus an aberration is generated, a variety of diseases, malformations and even death can be caused by the aberration.

With growth in genetics, functions of genes, correlations between genes and diseases, etc. are being revealed, diagnosis on gene mutations regarding specific diseases becomes possible and gene diagnosis is used in clinical treatment.

In such gene research, gene sequence search is essential.

Gene researchers have sequences for desired genes or bacteria. Gene researchers obtain new information, such as new or mutant viruses, through searching web sites updated frequently. The web sites may include the National Center for Biotechnology Information Basic Local Alignment Search Tool ("NCBI BLAST") and the European Bioinformatics Institute Basic Local Alignment Search Tool ("EBI BLAST").

However, when the conventional search method is used, there is inconvenience that a researcher must access an individual web site and separately search a desired gene sequence. Also, as the search result, only whether a desired gene sequence exists can be checked and no information regarding study trends in the biology field can be obtained. For example, through the conventional search method, there is provided no information about search frequency of gene sequences, different gene sequences in which researchers studying a specific gene sequence are interested, transition in search frequency of a specific gene sequence, etc.

BRIEF SUMMARY OF THE INVENTION

An exemplary embodiment provides a method for searching a gene sequence. The method provides a variety of information regarding a specific gene sequence so that study trends in the biology field can be understood.

An exemplary embodiment provides an apparatus for searching a gene sequence. The apparatus provides a variety of information regarding a specific gene sequence so that study trends in the biology field can be understood.

In an exemplary embodiment there is provided a method for searching a gene sequence. The method includes receiving the gene sequence to be searched from a user, generating extended sequences including the received gene sequence, partial sequences included in the gene sequence and an inverse sequence complementary to the gene sequence, storing the gene sequence, the extended sequences, the partial sequences, the inverse sequence and input-related record information in a database, integrated-searching the gene sequence using a gene sequence search server, estimating a gene sequence search ranking for a first predetermined period using the database and outputting an integrated and searched result of the gene sequence and a gene sequence search ranking result to the user. In an exemplary embodiment, the receiving the gene sequence includes receiving a second predetermined period for estimating the gene sequence search ranking and the estimating a gene sequence search ranking includes estimating the gene sequence search ranking for the second received predetermined period.

In an exemplary embodiment, the input-related record information may include user information, input region information and input time information.

In an exemplary embodiment, the integrated-searching the gene sequence includes additionally searching at least one of the extended sequences, the partial sequences, and the inverse sequence, other than the gene sequence.

In an exemplary embodiment, the estimating a gene sequence search ranking includes estimating a gene sequence search ranking for a region.

In an exemplary embodiment, the method further includes extracting search sequences of a different user from the database, the extracted search sequences including the received gene sequence. The outputting an integrated and searched result of the gene sequence and a gene sequence search ranking result includes additionally outputting extracted results.

In an exemplary embodiment, the method further includes extracting different search sequences of a different user from the database, the different user having searched the received gene sequence or a sequence including the received gene sequence. The outputting an integrated and searched result of the gene sequence and a gene sequence search ranking result includes additionally outputting extracted results.

The method further includes estimating transition in search frequency of the received gene sequence for a predetermined period using the database. The outputting an integrated and searched result of the gene sequence and a gene sequence search ranking result includes additionally outputting a transition result.

In an exemplary embodiment, the outputting an integrated and searched result of the gene sequence and a gene sequence search ranking result includes additionally outputting information related to the searched gene sequence or a gene sequence having a higher ranking.

In an exemplary embodiment, the related information may includes names of pathogens, mutant types, patent information and news information, regarding the gene sequence.

In an exemplary embodiment, there is provided an apparatus for searching a gene sequence. The apparatus includes an input unit receiving the gene sequence to be searched from a user, a related sequence generator generating extended sequences including the gene sequence, partial sequences included in the gene sequence and an inverse sequence complementary to the gene sequence, a database storing the gene sequence, the extended sequences, the partial sequences, the inverse sequence and input-related record information, an integrated search unit integrating and searching the gene sequence using a gene sequence search server, a search ranking estimator estimating a gene sequence search ranking for a first predetermined period using the database and an output unit outputting an integrated-searched result or a search ranking result of the gene sequence to the user.

In an exemplary embodiment, the input unit further receives a second predetermined period for estimating the gene sequence search ranking and the search ranking estimator estimates a search ranking for the received second predetermined period.

In an exemplary embodiment, the input-related record information may include user information, input region information and input time information.

In an exemplary embodiment, the integrated-search unit additionally searches at least one of the extended sequences, the partial sequences and the inverse sequence, other than the gene sequence.

In an exemplary embodiment, the search ranking estimator estimates a search ranking for a region.

In an exemplary embodiment, the apparatus further includes a first search sequence extractor extracting search sequences of a different user from the database, the extracted search sequences including the received gene sequence. The output unit additionally outputs extracted results.

In an exemplary embodiment, the apparatus further includes a second search sequence extractor extracting different search sequences of a different user from the database, the different user having searched the received gene sequence and a sequence including the received gene sequence. The output unit additionally outputs extracted results.

In an exemplary embodiment, the apparatus further includes a search transition estimator estimating transition in search frequency of the received gene sequence for a third predetermined period using the database. The output unit additionally outputs the transition result.

In an exemplary embodiment, the output unit additionally outputs information related to the searched gene sequence or a gene sequence having a ranking.

In an exemplary embodiment, the related information may include names of pathogens, mutant types, patent information, and news information, regarding the gene sequence.

BRIEF DESCRIPTION OF THE DRAWINGS

The above and other features and advantages of the present invention will become more apparent by describing in detail exemplary embodiments thereof with reference to the attached drawings in which:

FIG. 3 shows an exemplary embodiment of a display including an output result of a gene sequence search apparatus search according to the present invention. Sequences shown having a rank of 1 to 10 correspond to SEQ ID NOS: 6-15 respectively;

FIG. 4 shows another exemplary embodiment of a display including an output result of a gene sequence search apparatus search according to the present invention. Sequences shown having a RANK of 1 to 10 in the Table "Top 10 RANKS", correspond to SEQ ID NOS: 6-15 respectively. The sequence shown having a RANK of 3 in the Table "Related Searches" corresponds to SEQ ID NO:16. The input gene sequence CTTGACTGCGA (Related Searches and Current search) corresponds to SEQ ID NO: 5.

DETAILED DESCRIPTION OF THE INVENTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, embodiments of the present invention will be described in detail with reference to the appended drawings.

Figure 1:
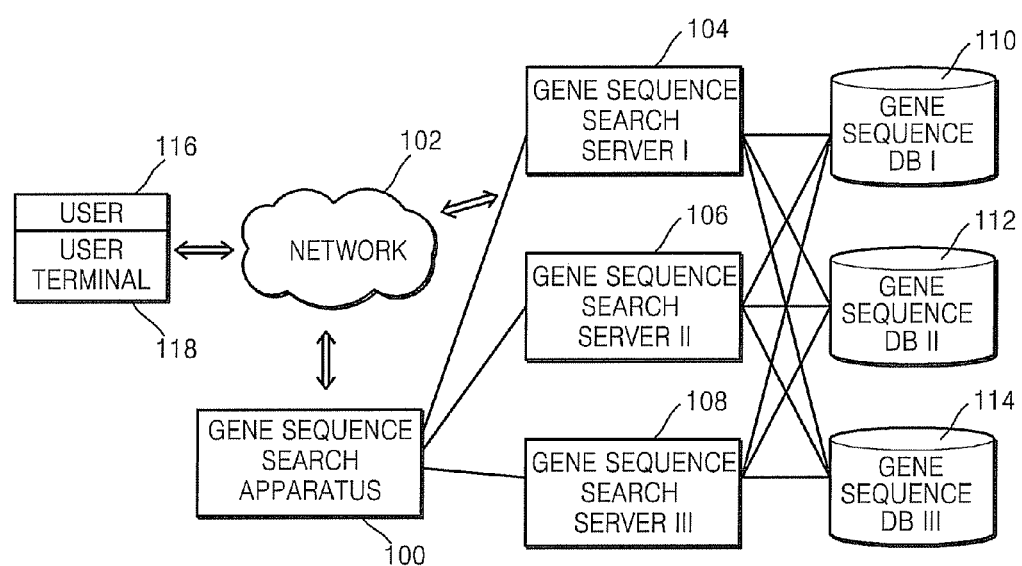
FIG. 1 is a schematic view illustrating an exemplary embodiment of a network connection of a gene sequence search apparatus according to the present invention.

FIG. 1 is a schematic view illustrating an exemplary embodiment of a network connection of a gene sequence search apparatus 100 according to the present invention.

Referring to FIG. 1, the gene sequence search apparatus 100 is connected to at least one user terminal 118 and one or more gene sequence search servers 104, 106 and 108 through a network 102.

In an exemplary embodiment, the one or more gene sequence search servers 104, 106, and 108 may be a search engine server, etc. The gene sequence search servers 104, 106, and 108 support searching for a gene sequence by a user 116 wanting to obtain the gene sequence from one or more gene sequence databases 110, 112, and 114.

In exemplary embodiments, a search tool used by the gene sequence search servers 104, 106, and 108 may be a program, such as Basic Local Alignment Search Tool ("BLAST"), FASTA, and/or Smith-Waterman algorithm. The gene sequence databases 110, 112, and 114 may be databases provided by National Center for Biotechnology Information (NCBI), Swiss Institute of Bioinformatics (SIB) and/or European Bioinformatics Institute (EBI).

The user 116 has a user terminal 118 for accessing the gene sequence search servers 104, 106, and 108. If the user 116 inputs a gene sequence which he or she wants to search to a search word input blank of the gene sequence search apparatus 100 through the user terminal 118, he or she can obtain an integrated search result from the gene sequence search servers 104, 106, and 108 and understand study trends in the biology field.

As illustrated in FIG. 1, the user terminal 118 is connected to the gene sequence search apparatus 100 through the network 102. The network 102 may be, but is not limited to, the Internet. The user terminal 118 may display a result provided by the gene sequence search apparatus 100. In exemplary embodiments, the user terminal 118 may be a terminal, such as a personal computer, a handheld computer, a Personal Digital Assistant ("PDA"), an MP3 player, an electronic dictionary, a cellular phone, a smart phone, etc., having a predetermined memory device and in which a predetermined microprocessor is installed so as to have a predetermined calculation function.

Figure 2:
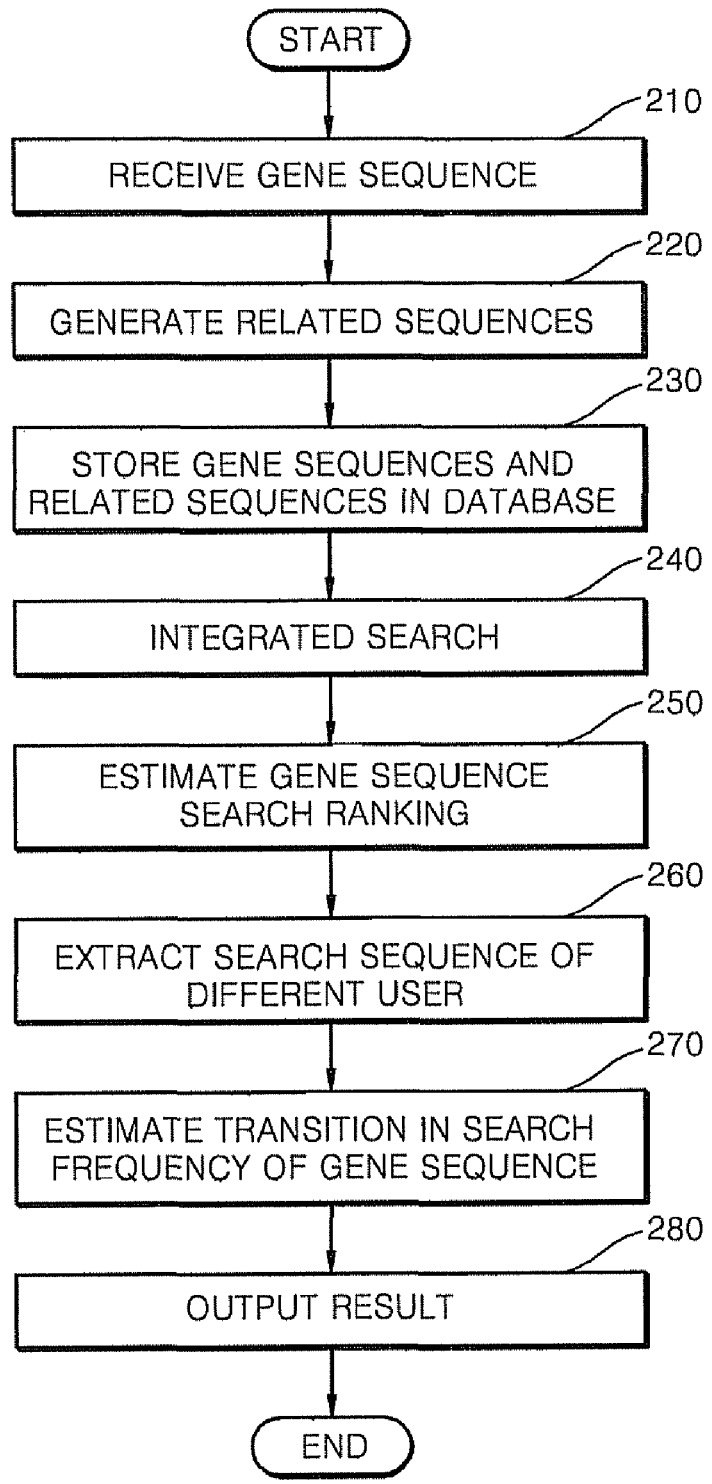
FIG. 2 is a flowchart illustrating an exemplary embodiment of a gene sequence search method according to the present invention.

FIG. 2 is a flowchart illustrating an exemplary embodiment of a gene sequence search method according to the present invention.

Referring to FIG. 2, a gene sequence to be searched is received from a user (operation 210). In exemplary embodiments, then the user inputs the gene sequence, he or she can additionally input different search conditions. In one exemplary embodiment, if the user wants to obtain a search ranking result for a predetermined period, he or she can input the predetermined period. Also, if the user wants to know a search ranking result for a specific region, he or she can input the specific region.

Sequences related to the input gene sequence are created (operation 220). In exemplary embodiments, the related sequences may include, but are not limited to, extended sequences including the input gene sequence, partial sequences included in the gene sequence and/or an inverse sequence complementary to the gene sequence. In one exemplary embodiment, if the input gene sequence is 'agtcaacgttaag' (SEQ ID NO. 1), one of the extended sequences may be 'ttacagtcaacgttaagtacg' (SEQ ID NO. 2), one of the partial sequences may be 'aacgtt' (SEQ ID NO. 3), and the inverse sequence may be 'tcagttgcaattc' (SEQ ID NO. 4).

The related sequences, such as the gene sequence, the extended sequences, the partial sequences, the inverse sequence, and input-related record information are stored in a database (operation 230). The input-related record information may include user information, input region information and input time information. The input-related record information is used as basic data in the following statistical processing operation.

An integrated search is performed using at least one gene sequence search server (operation 240). The input gene sequence is input to an integrated search server, searching is performed in the integrated search server and the searched results are integrated. In an exemplary embodiment, at least one of the extended sequences, the partial sequences and the inverse sequence other than the gene sequence can be additionally searched. The one or more gene sequence search servers may be web servers, which use a search tool, such as BLAST, FASTA, or Smith-Waterman algorithm, and in which a database provided by NCBI, SIB, or EBI is installed.

A gene sequence search ranking for a predetermined period is calculated using the database (operation 250). If another predetermined period for calculating a gene sequence search ranking is additionally input by the user when the gene sequence is input, a search ranking for the input predetermined period is calculated in operation 250. Also, in operation 250, a search ranking for each region can be calculated. In one exemplary embodiment, a search ranking for each country can be calculated using an access IP domain.

A gene sequence search ranking searched by different users is extracted from the database (operation 260). In an exemplary embodiment, search sequences of a different user, including the input gene sequence, can be extracted. Also, it is possible to extract different search sequences of different users that have searched the input gene sequence or a sequence including the input gene sequence. Through the extracted search sequences of the different users, the user can understand the whole study trends in the current biology field.

Transition in search frequency of the input gene sequence for a predetermined period is estimated using the database (operation 270). In one exemplary embodiment, transition in a search ranking regarding a specific gene sequence for recent three months is estimated.

The integrated search result and/or search ranking result of the gene sequence is output to the user (operation 280). In an exemplary embodiment, the sequence search results and/or sequence search ranking results of different users, other than the integrated search result or search ranking result of the input gene sequence, can be additionally output to the user in operation 280.

In an exemplary embodiment, in operation 280, information related to the searched gene sequence or a gene sequence having a search ranking can be additionally output. The related information may include, but is not limited to, names of pathogens, mutant types, patent information and/or news information, regarding the sequence.

FIG. 3 shows an exemplary embodiment of a display including an output result of a gene sequence search apparatus according to the present invention.

Referring to FIG. 3, ten (10) gene sequences having higher search rankings are arranged in an order and the number of searches and a recent search time for each gene sequence are provided.

FIG. 4 shows another exemplary embodiment of a display including an output result of a gene sequence search apparatus according to the present invention.

Referring to FIG. 4, other than the search rankings of the ten (10) gene sequences as illustrated in FIG. 3, gene sequences searched previously by different users which have searched the input gene sequence 'cttgactgcga' (SEQ ID NO. 5) or a sequence including the input gene sequence 'cttgactgcga' (SEQ ID NO. 5) are provided together with the search rankings. On the lower portion of the screen, a result integrated and searched using the gene sequence search server is provided.

Figure 5:
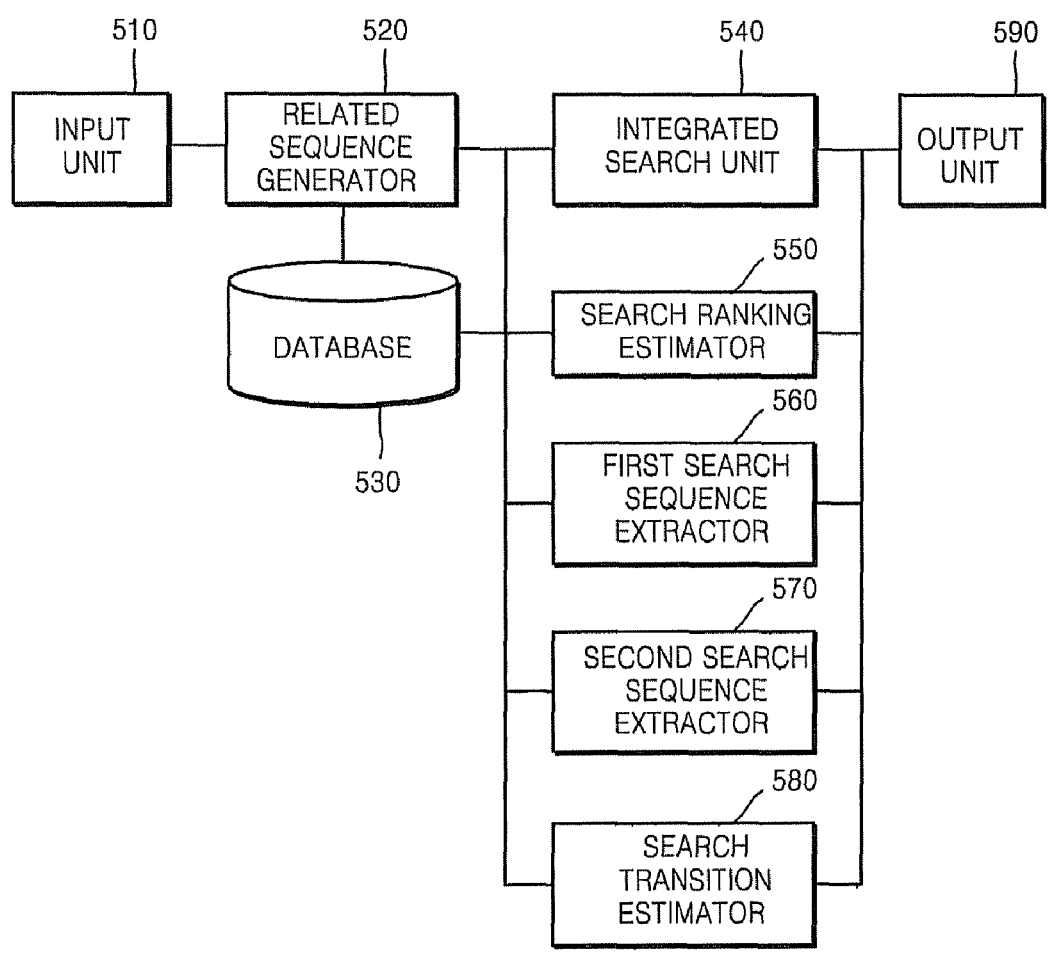
FIG. 5 is a block diagram of an exemplary embodiment of a gene sequence search apparatus according to the present invention.

FIG. 5 is a block diagram of an exemplary embodiment of a gene sequence search apparatus according to the present invention.

Referring to FIG. 5, the gene sequence search apparatus includes an input unit 510, a related-sequence generator 520, a database 530, an integrated search unit 540, a search ranking estimator 550, a first search sequence extractor 560, a second search sequence extractor 570, a search transition estimator 580 and an output unit 590.

The input unit 510 receives a gene sequence to be searched from a user. When the user inputs the gene sequence, he or she can additionally input different search conditions. In one exemplary embodiment, if the user wants to know a search ranking result for a predetermined period, he or she can input the predetermined period. If the user wants to know search trends of a specific region, he or she can input the specific region.

In exemplary embodiments, the input unit 510 can provide a correct search result by temporarily storing gene sequences searched frequently by each user and/or can perform a separate management by temporarily storing a history or frequency count, etc. for a gene sequence input by the user.

The related sequence generator 520 generates sequences related to the input gene sequence. The related sequences may include, but are not limited to, extended sequences including the input gene sequence, partial sequences included in the gene sequence and an inverse sequence complementary to the gene sequence.

The database 530 stores the gene sequence, the extended sequences, the partial sequences, the inverse sequence and input-related record information. The input-related record information can include user information, input region information and/or input time information. The input-related record information is used as basic data in the following statistical processing operation.

The integrated search unit 540 performs integrated search using one or more gene sequence search servers. The input gene sequence is input to an integrated search server and search and integration are performed in the integrated search server. In an exemplary embodiment, at least one of the extended sequences, the partial sequences, and the inverse sequence, other than the gene sequence, can be additionally searched. The one or more gene sequence search servers may be web servers which use a search tool, such as BLAST, FASTA, or Smith-Waterman algorithm and in which a database provided by NCBI, SIB, or EBI is installed.

The search ranking estimator 550 estimates a gene sequence search ranking for a predetermined period using the database. If another predetermined period for estimating a gene sequence search ranking is additionally input to the input unit 510, the search ranking estimator 550 estimates a search ranking for the input predetermined period. The search ranking estimator 550 can estimate a search ranking for each region, such as estimating a search ranking for countries using an access IP domain.

The first search sequence estimator 560 extracts search sequences of different users, including the input gene sequence, from the database.

The second search sequence extractor 570 extracts different search sequences of different users that have searched the input gene sequence or a sequence including the input gene sequence, from the database.

The search transition estimator 580 estimates a search transition for the input gene sequence for the predetermined period, using the database. In one exemplary embodiment, a search ranking change for a specific gene sequence during recent three months can be estimated.

The output unit 590 outputs the integrated search result and/or search ranking result of the gene sequence to the user. The output unit 590 can additionally output the search sequence results or sequence search transition results of different users, other than the integrated search result or search ranking result of the gene sequence, to the user.

In an exemplary embodiment, the output unit 590 can additionally output information related to the searched gene sequence or a gene sequence having a higher ranking. The related information may be names of pathogens, mutant types, patent information, and news information, regarding the sequence.

The invention can also be embodied as computer readable codes on a computer readable recording medium. The computer readable recording medium may be any of a number of data storage devices that store data which can be thereafter read by a computer system. Exemplary embodiments of the computer readable recording medium include read-only memory ("ROM"), random-access memory ("RAM"), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion.

As in the illustrated exemplary embodiments, by performing integrated search using a plurality of conventional gene sequence search servers, it is possible to conveniently obtain a variety of information about a specific gene sequence through one search. Also, by providing information, such as a higher gene sequence search ranking, a change in the higher gene sequence search ranking, different gene sequences searched by different users that have searched a specific gene sequence, etc., a user can understand study trends in the biology field through the one search. Also, by using the searched results, it is possible to monitor a degree of interest in the biology field about whether mutation exists at which part of a specific gene sequence, where an important part in a conventional virus sequence is, or where a mutation sequence part of a new virus is.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for searching a gene sequence, the method comprising:

on a gene sequence search apparatus,
receiving the gene sequence from a user;
generating extended sequences of the received gene sequence, partial sequences included in the gene sequence and an inverse sequence complementary to the gene sequence;
storing the gene sequence, the extended sequences, the partial sequences, the inverse sequence and input-related record information in a database;
performing an integrated search using an integrated search server by inputting the gene sequence to the integrated search server;
estimating a gene sequence search ranking of a first predetermined period, wherein the estimating is performed using the database;
integrating and storing an integrated search result of the gene sequence and a gene sequence search ranking result in the database; and
outputting the integrated search result of the gene sequence and the gene sequence search ranking result to the user.

2. The method of claim 1, wherein the receiving the gene sequence comprises receiving a second predetermined period and the estimating a gene sequence search ranking comprises estimating the gene sequence search ranking of the received second predetermined period.

3. The method of claim 1, wherein the input-related record information comprises user information, input region information, input time information or a combination comprising at least one of the foregoing.

4. The method of claim 1, wherein performing an integrated search comprises additionally searching at least one of the extended sequences, the partial sequences and the inverse sequence, other than the gene sequence.

5. The method of claim 1, wherein the estimating a gene sequence search ranking comprises estimating a gene sequence search ranking for a region.

6. The method of claim 1, further comprising extracting search sequences of a different user from the database, the extracted search sequences comprising the received gene sequence, wherein the outputting an integrated and searched result of the gene sequence and a gene sequence search ranking result comprises additionally outputting extracted results.

7. The method of claim 1, further comprising extracting different search sequences of a different user from the database, the different user having searched the received gene sequence or a sequence comprising the received gene sequence, wherein the outputting an integrated and searched result of the gene sequence and a gene sequence search ranking result comprises additionally outputting extracted results.

8. The method of claim 1, further comprising estimating transition in search frequency of the received gene sequence for a third predetermined period using the database, wherein the outputting an integrated and searched result of the gene sequence and a gene sequence search ranking result comprises additionally outputting a transition result.

9. The method of claim 1, wherein the outputting of the integrated and searched result of the gene sequence and the gene sequence search ranking result comprises additionally outputting information related to the searched gene sequence or a gene sequence having a higher ranking.

10. The method of claim 9, wherein the related information comprises names of pathogens, mutant types, patent information, news information, regarding the gene sequence, or a combination comprising at least one of the foregoing.

11. An apparatus for searching a gene sequence, the apparatus comprising:

an input unit for receiving the gene sequence from a user;
a related sequence generator for generating extended sequences comprising the gene sequence, partial sequences included in the gene sequence and an inverse sequence complementary to the gene sequence;
a database for storing the gene sequence, the extended sequences, the partial sequences, the inverse sequence and input-related record information;
an integrated search unit for integrating and searching one or more gene sequence search servers using the gene sequence;
a search ranking estimator for estimating a gene sequence search ranking of a first predetermined period, wherein the estimating is performed using the database; and
an output unit for outputting an integrated-searched result, a search ranking result of the gene sequence, or the integrated-searched result and the search ranking result of the gene sequence to the user.

12. The apparatus of claim 11, wherein the input unit further receives a second predetermined period used in the estimating a gene sequence search ranking and the search ranking estimator estimates a search ranking of the second received predetermined period.

13. The apparatus of claim 11, wherein the input-related record information comprises user information, input region information, input time information or a combination comprising at least one of the foregoing.

14. The apparatus of claim 11, wherein the integrated-search unit additionally searches at least one of the extended sequences, the partial sequences and the inverse sequence, other than the gene sequence.

15. The apparatus of claim 11, wherein the search ranking estimator estimates a search ranking for each region.

16. The apparatus of claim 11, further comprising a first search sequence extractor extracting search sequences of a different user from the database, the extracted search sequences comprising the received gene sequence, wherein the output unit additionally outputs extracted results.

17. The apparatus of claim 11, further comprising a second search sequence extractor extracting different search sequences of a different user from the database, the different user having searched the received gene sequence and a sequence comprising the received gene sequence, wherein the output unit additionally outputs extracted results.

18. The apparatus of claim 11, further comprising a search transition estimator estimating transition in search frequency of the received gene sequence for a third predetermined period using the database, wherein the output unit additionally outputs a transition result.

19. The apparatus of claim 11, wherein the output unit additionally outputs information related to the searched gene sequence or a gene sequence having a ranking.

20. The apparatus of claim 19, wherein the related information comprises names of pathogens, mutant types, patent information, news information regarding the gene sequence or a combination comprising at least one of the foregoing.

21. A computer-readable recording medium storing a computer program executing the method of claim 1, wherein the computer readable recording medium is a device to store computer readable data.

22. The computer-readable recording medium of claim 21, wherein the device consists of a read-only memory (ROM), a random-access memory (RAM), a CD-ROM, a magnetic tape, a floppy disk, or an optical data storage device.

* * * * *

SEQUENCE LISTING

```
<160> NUMBER OF SEQ ID NOS: 16

<210> SEQ ID NO 1
<211> LENGTH: 13
<212> TYPE: DNA
<213> ORGANISM: Artificial Sequence
<220> FEATURE:
<223> OTHER INFORMATION: input gene sequence

<400> SEQUENCE: 1
agtcaacgtt aag                                                    13

<210> SEQ ID NO 2
<211> LENGTH: 21
```

```
<212> TYPE: DNA
<213> ORGANISM: Artificial Sequence
<220> FEATURE:
<223> OTHER INFORMATION: chemically synthesized

<400> SEQUENCE: 2
ttacagtcaa cgttaagtac g                                              21

<210> SEQ ID NO 3
<211> LENGTH: 6
<212> TYPE: DNA
<213> ORGANISM: Artificial Sequence
<220> FEATURE:
<223> OTHER INFORMATION: chemically synthesized

<400> SEQUENCE: 3 aacgtt                                                                6

<210> SEQ ID NO 4
<211> LENGTH: 13
<212> TYPE: DNA
<213> ORGANISM: Artificial Sequence
<220> FEATURE:
<223> OTHER INFORMATION: chemically synthesized

<400> SEQUENCE: 4
tcagttgcaa ttc                                                       13

<210> SEQ ID NO 5
<211> LENGTH: 11
<212> TYPE: DNA
<213> ORGANISM: Artificial Sequence
<220> FEATURE:
<223> OTHER INFORMATION: input gene sequence

<400> SEQUENCE: 5
cttgactgcg a                                                         11

<210> SEQ ID NO 6
<211> LENGTH: 18
<212> TYPE: DNA
<213> ORGANISM: Unknown
<220> FEATURE:
<223> OTHER INFORMATION: output gene sequence

<400> SEQUENCE: 6
accaaagagt gatactca                                                  18

<210> SEQ ID NO 7
<211> LENGTH: 23
<212> TYPE: DNA
<213> ORGANISM: Unknown
<220> FEATURE:
<223> OTHER INFORMATION: output gene sequence

<400> SEQUENCE: 7
ataagctagc ttgactgcga gcg                                            23

<210> SEQ ID NO 8
<211> LENGTH: 8
<212> TYPE: DNA
<213> ORGANISM: Unknown
<220> FEATURE:
<223> OTHER INFORMATION: output gene sequence

<400> SEQUENCE: 8 ttaaacct                                                              8
```

<210> SEQ ID NO 9
<211> LENGTH: 20
<212> TYPE: DNA
<213> ORGANISM: Unknown
<220> FEATURE:
<223> OTHER INFORMATION: output gene sequence

<400> SEQUENCE: 9
ctgcgagacg gacaagtcga                                               20

<210> SEQ ID NO 10
<211> LENGTH: 23
<212> TYPE: DNA
<213> ORGANISM: Unknown
<220> FEATURE:
<223> OTHER INFORMATION: output gene sequence

<400> SEQUENCE: 10
acaggttggt ccctatctat tgt                                           23

<210> SEQ ID NO 11
<211> LENGTH: 23
<212> TYPE: DNA
<213> ORGANISM: Unknown
<220> FEATURE:
<223> OTHER INFORMATION: output gene sequence

<400> SEQUENCE: 11
accaaagagt gatactcagg aga                                           23

<210> SEQ ID NO 12
<211> LENGTH: 10
<212> TYPE: DNA
<213> ORGANISM: Unknown
<220> FEATURE:
<223> OTHER INFORMATION: output gene sequence

<400> SEQUENCE: 12
ctatctattg                                                          10

<210> SEQ ID NO 13
<211> LENGTH: 11
<212> TYPE: DNA
<213> ORGANISM: Unknown
<220> FEATURE:
<223> OTHER INFORMATION: output gene sequence

<400> SEQUENCE: 13
cttgactgcg a                                                        11

<210> SEQ ID NO 14
<211> LENGTH: 2
<212> TYPE: DNA
<213> ORGANISM: Unknown
<220> FEATURE:
<223> OTHER INFORMATION: output gene sequence

<400> SEQUENCE: 14 tt                                                                   2

<210> SEQ ID NO 15
<211> LENGTH: 2
<212> TYPE: DNA
<213> ORGANISM: Unknown
<220> FEATURE:
<223> OTHER INFORMATION: output gene sequence

```
<400> SEQUENCE: 15 ct                                                                    2

<210> SEQ ID NO 16
<211> LENGTH: 15
<212> TYPE: DNA
<213> ORGANISM: Unknown
<220> FEATURE:
<223> OTHER INFORMATION: output gene sequence

<400> SEQUENCE: 16
gcttgactgc gagcg                                                     15
```